(12) United States Patent
Baumgart et al.

(10) Patent No.: US 8,849,375 B2
(45) Date of Patent: Sep. 30, 2014

(54) SYSTEM FOR DETECTING ROTATION ANGLE OF A CATHETER IN AN X-RAY IMAGE

(75) Inventors: John Baumgart, Hoffman Estates, IL (US); Guang Yang, Hoffman Estates, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 129 days.

(21) Appl. No.: 13/532,953

(22) Filed: Jun. 26, 2012

(65) Prior Publication Data

US 2013/0109959 A1 May 2, 2013

Related U.S. Application Data

(60) Provisional application No. 61/554,042, filed on Nov. 1, 2011, provisional application No. 61/554,032, filed on Nov. 1, 2011.

(51) Int. Cl.
| | |
|---|---|
| *A61B 5/05* | (2006.01) |
| *A61B 8/00* | (2006.01) |
| *A61B 6/00* | (2006.01) |
| *A61B 8/12* | (2006.01) |
| *A61B 6/12* | (2006.01) |

(52) U.S. Cl.
CPC ............... *A61B 6/12* (2013.01); *A61B 8/4254* (2013.01); *A61B 8/4263* (2013.01); *A61B 8/463* (2013.01); *A61B 6/425* (2013.01); *A61B 8/12* (2013.01)
USPC .......................................................... 600/424

(58) Field of Classification Search
CPC ...... A61B 8/12; A61B 8/4254; A61B 8/4263; A61B 8/463; A61B 6/12; A61B 6/425; A61B 5/0062; A61B 5/0066; A61B 5/0084; A61B 5/01; A61B 5/02007; A61B 5/6852; A61B 5/6853; A61B 5/6885; A61M 1/101; A61M 2001/1024; A61M 2001/1034; A61M 2001/125; F04D 29/242; F04D 3/02; F04D 29/188
USPC .......................................................... 600/424
See application file for complete search history.

(56) References Cited

U.S. PATENT DOCUMENTS 5,630,806 A * 5/1997 Inagaki et al. ................ 604/524
5,771,895 A * 6/1998 Slager .......................... 600/462

(Continued)

OTHER PUBLICATIONS

Co-pending U.S. Appl. No. 13/532,897, filed Jun. 26, 2012.

*Primary Examiner* — Long V. Le
*Assistant Examiner* — Bo J Peng
(74) *Attorney, Agent, or Firm* — Brennan K Bradley

(57) ABSTRACT

An IVUS catheter is advantageously provided with a particular radio-opaque pattern enabling detection of catheter rotation angle with respect to an X-ray imaging source for co-registering IVUS image data with angiographic X-ray or CT image data, for example. An ultrasound catheter system supports orientation and display of intra-vascular ultrasound imaging data. The system comprises an ultrasound catheter for acquiring ultrasound images comprising a body having a pattern of radio-opaque material on the external surface of the catheter body. The pattern varies with angular rotation of the catheter and indicates an angle of rotation of a predetermined reference orientation of the catheter relative to an X-ray radiation source, so that an X-ray image of the catheter body indicates the pattern and the pattern is analyzable by an image data processor to determine the angle of rotation.

14 Claims, 6 Drawing Sheets

(56) References Cited

U.S. PATENT DOCUMENTS

| | | |
|---|---|---|
| 6,612,992 B1 | 9/2003 | Hossack et al. |
| 7,996,060 B2 | 8/2011 | Trofimov et al. |
| 8,057,394 B2 | 11/2011 | Dala-Krishna |
| 2006/0135870 A1* | 6/2006 | Webler .......................... 600/431 |
| 2006/0285638 A1* | 12/2006 | Boese et al. .................... 378/62 |
| 2008/0146941 A1 | 6/2008 | Dala-Krishna |
| 2009/0052614 A1* | 2/2009 | Hempel et al. .................. 378/8 |
| 2010/0094125 A1 | 4/2010 | Younge et al. |
| 2011/0238083 A1 | 9/2011 | Moll et al. |
| 2012/0004668 A1 | 1/2012 | Wallace et al. |
| 2012/0113108 A1 | 5/2012 | Dala-Krishna |

* cited by examiner

SYSTEM FOR DETECTING ROTATION ANGLE OF A CATHETER IN AN X-RAY IMAGE

This is a non-provisional application of provisional application Ser. No. 61/554,042 filed Nov. 1, 2011, by J. Baumgart et al. and of provisional application Ser. No. 61/554,032 filed Nov. 1, 2011, by J. Baumgart et al.

FIELD OF THE INVENTION

This invention concerns an ultrasound catheter having a pattern of radio-opaque material on the external surface of the catheter body that varies with angular rotation of the catheter and indicates an angle of rotation of a predetermined reference orientation of the catheter relative to an X-ray radiation source.

BACKGROUND OF THE INVENTION

Intravascular Ultrasound (IVUS) imaging produces a series of tomographic views of a patient vessel as a catheter is pulled through the vessel, but displayed data lacks information regarding the orientation of these views with respect to actual patient anatomy. In applications where there is a co-registration of IVUS data with data showing vessel morphology, displaying IVUS images that are not necessarily oriented to this morphology can be confusing or misleading and impedes diagnosis of patient medical conditions. A system according to invention principles addresses this deficiency and related problems.

SUMMARY OF THE INVENTION

An IVUS catheter is advantageously provided with a particular radio-opaque pattern enabling detection of catheter rotation angle with respect to an X-ray imaging source for use in co-registering IVUS image data with angiographic X-ray or CT image data, for example. An ultrasound catheter system supports orientation and display of intra-vascular ultrasound imaging data. The system comprises an ultrasound catheter for acquiring ultrasound images comprising a body having a pattern of radio-opaque material on the external surface of the catheter body. The pattern varies with angular rotation of the catheter and indicates an angle of rotation of a predetermined reference orientation of the catheter relative to an X-ray radiation source, so that an X-ray image of the catheter body indicates the pattern and the pattern is analyzable by an image data processor to determine the angle of rotation.

DETAILED DESCRIPTION OF THE INVENTION

Figure 2:
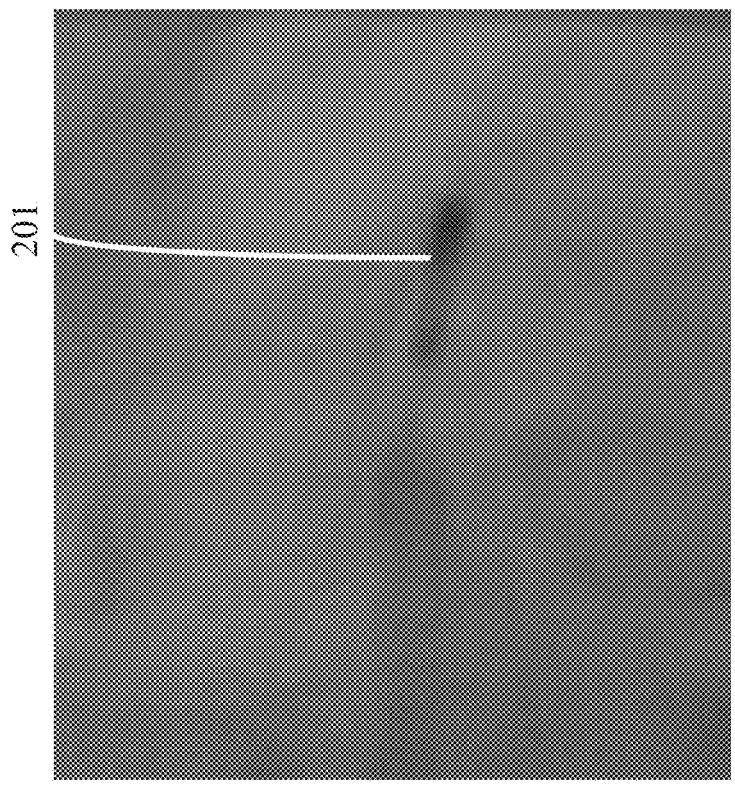
FIG. 2 shows a known common IVUS catheter that is symmetric in shape and appears on an X-ray image as a solid rod shape.

A system detects a rotation angle of a catheter to provide orientation information for aligning intravascular ultrasound (IVUS) images acquired by a catheter during advancement or retraction of the catheter in a vessel, for example. An IVUS catheter is shown in an X-ray image and is advantageously provided with a particular radio-opaque pattern enabling detection of catheter rotation angle with respect to an X-ray imaging source. The rotation angle information is of particular use in co-registering IVUS image data with correctly oriented patient anatomy in an angiographic X-ray or CT image, for example. FIG. 2 shows a known common IVUS catheter 201 that is symmetric in shape and appears on an X-ray image as a solid rod shape. Catheters may also have an asymmetric shape so that appearance of a catheter in an X-ray image varies with twist or rotation angle. The system advantageously provides a radio-opaque pattern enabling detection of a twist (rotation) angle in an X-ray image.

The system detects a rotation angle of a catheter to provide orientation information for rotationally aligning intravascular ultrasound (IVUS) images acquired by a catheter during advancement or retraction of the catheter in a vessel, for example. IVUS Catheters display in X-ray images and are advantageously provided with a particular radio-opaque pattern enabling detection of catheter rotation angle with respect to the X-ray imaging source. The rotation angle information is of particular use in co-registering IVUS image data with angiographic X-ray or CT image data and showing consistently and correctly oriented patient anatomy. The system orients Intravascular Ultrasound (IVUS) image data to provide a consistent orientation with respect to patient anatomy and an external signal, such as an X-ray pulse or electromagnetic field. Oriented IVUS image data is co-registered with angiographic X-ray or CT image data that shows patient anatomy in known orientation. The system advantageously correlates orientation data with IVUS images used for display. The orientation is derived from one or more different sources, including, for example, orientation detected by an IVUS catheter during catheter pullback and orientation detected by analysis of X-ray frames acquired during the pullback.

Figure 1:
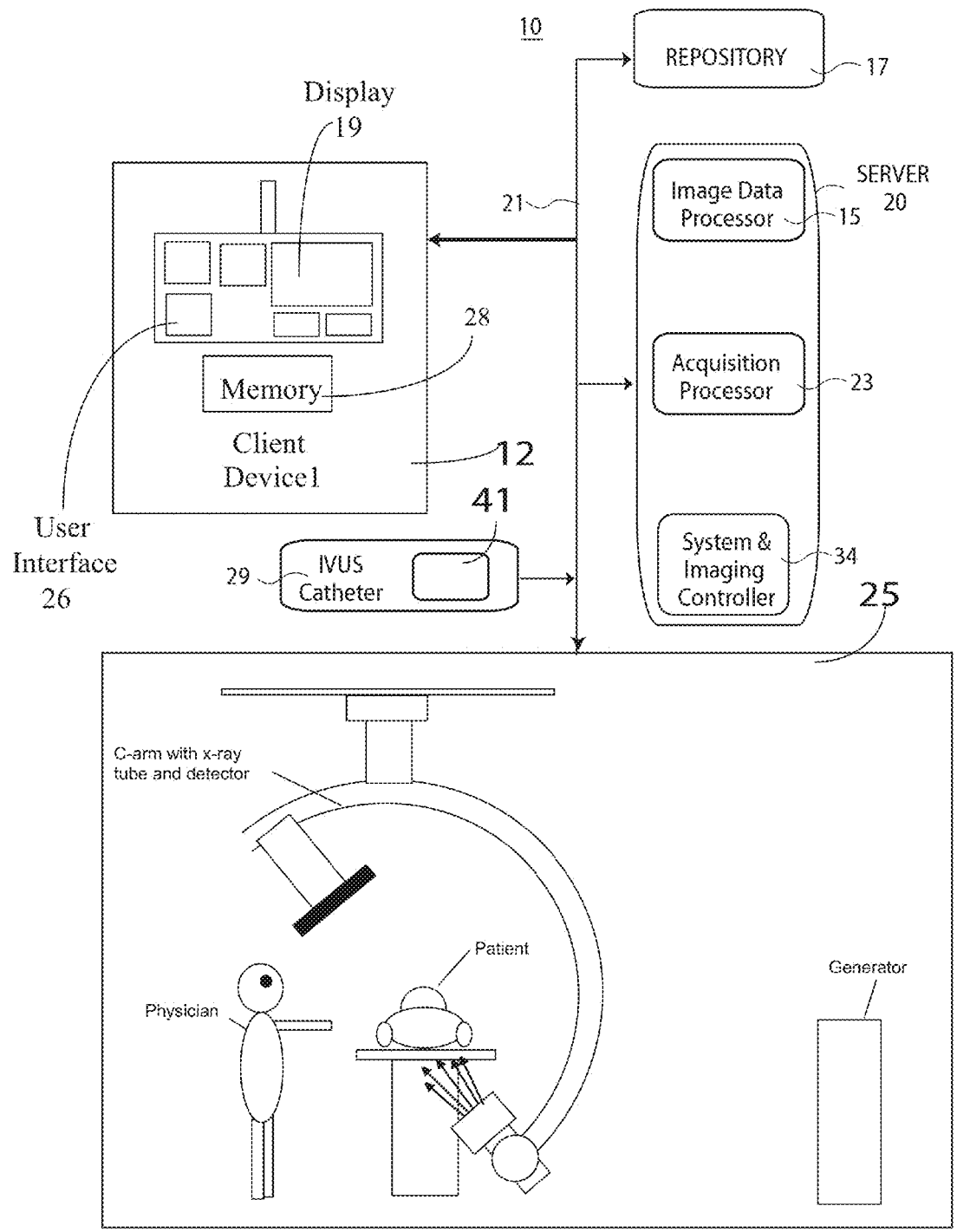
FIG. 1 shows an ultrasound catheter system supporting orientation and display of intra-vascular ultrasound imaging data, according to invention principles.

FIG. 1 shows an ultrasound catheter system 10 supporting orientation and display of intra-vascular ultrasound imaging data. System 10 includes one or more processing devices (e.g., workstations, computers or portable devices such as notebooks, Personal Digital Assistants, phones) 12 that individually include memory 28, a user interface 26 enabling user interaction with a Graphical User Interface (GUI) and display 19 supporting GUI and medical image presentation in response to predetermined user (e.g., physician) specific preferences. System 10 also includes at least one repository 17, server 20, IVUS catheter 29 and imaging device 25. Server 20 includes image data processor 15, acquisition processor 23 and system and imaging control unit 34. System and imaging control unit 34 controls operation of one or more imaging devices 25 for performing image acquisition of patient anatomy in response to user command Imaging devices 25 may comprise a mono-plane or biplane X-ray imaging system. The units of system 10 intercommunicate via network 21. At least one repository 17 stores X-ray and IVUS medical images and studies for patients in DICOM compatible (or other) data format. A medical image study individually includes multiple image series of a patient anatomical portion which in turn individually include multiple images.

Ultrasound catheter 29 acquires ultrasound images and has a body having a pattern 41 of radio-opaque material. The pattern may be located on the external surface of the catheter body or internally or at another location of the catheter body. The pattern varies with angular rotation of the catheter and indicates an angle of rotation of a predetermined reference orientation of the catheter relative to an X-ray radiation source of imaging system 25, so that an X-ray image of the catheter body indicates pattern 41 and the pattern is analyzable by image data processor 15 to determine the angle of rotation.

The orientation of IVUS catheter 29 is determined from X-ray images of the catheter advantageously including a radio-opaque marker varying around the circumference enabling determination of catheter orientation by presenting a unique 2-dimensional X-ray profile at different catheter rotational angle. Image data processor 15 determines orientation using this profile. For display of tomographic slices, a catheter orientation angle is determined and used to either automatically rotate the IVUS images to match the vascular morphology as seen from an external view, such as in an angiographic X-ray, or to automatically indicate on the IVUS image the direction of the signal source.

Figure 3:
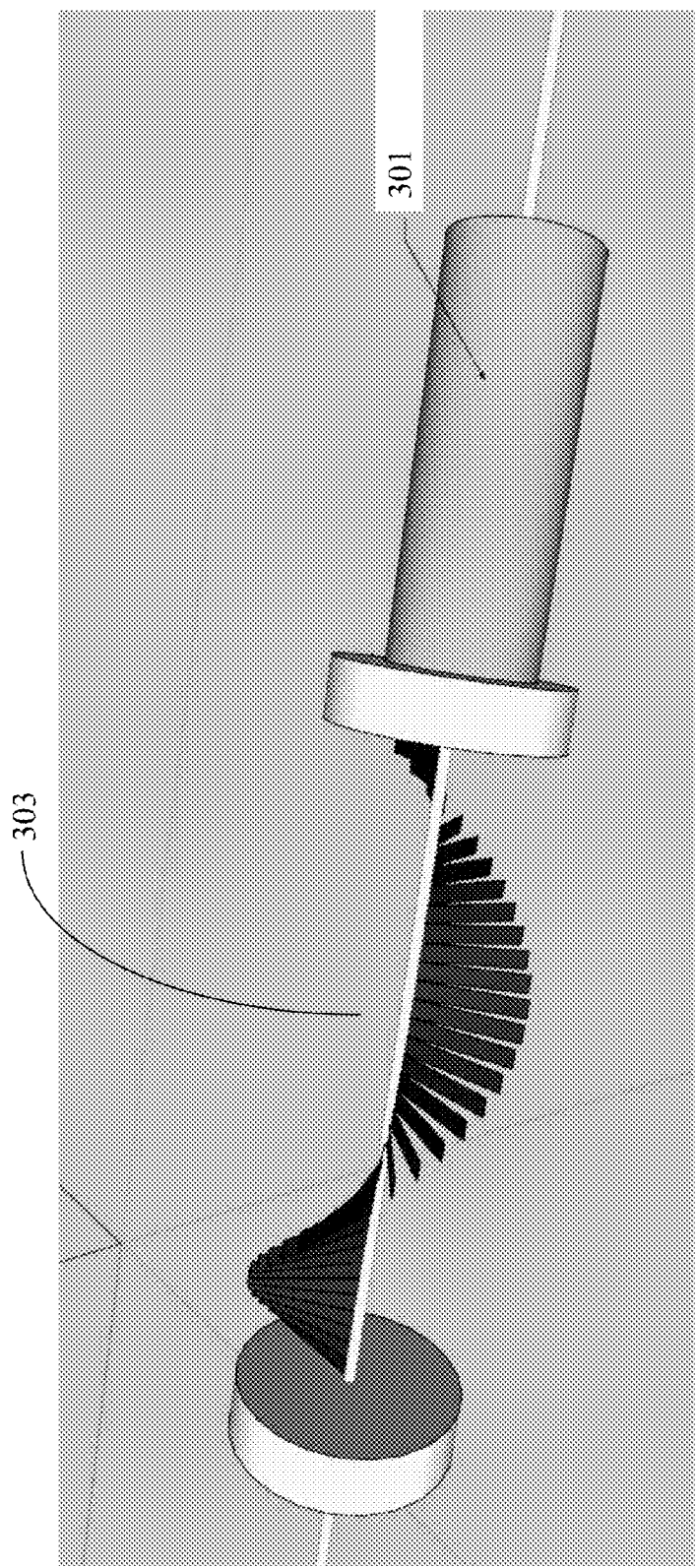
FIG. 3 shows an embodiment of a catheter twist-indicating pattern comprising a helical staircase-like pattern, according to invention principles.

FIG. 3 shows an embodiment of a catheter having IVUS transducer 301 and twist-indicating pattern 303 comprising a helical staircase-like pattern. The helical staircase-like pattern 303 of radiodense material comprises a twist indicator, so the catheter when twisted through different angles appears differently in an X-ray image. The system determines the catheter twist angle from the pattern automatically identified in a resultant X-ray image.

Figure 4:
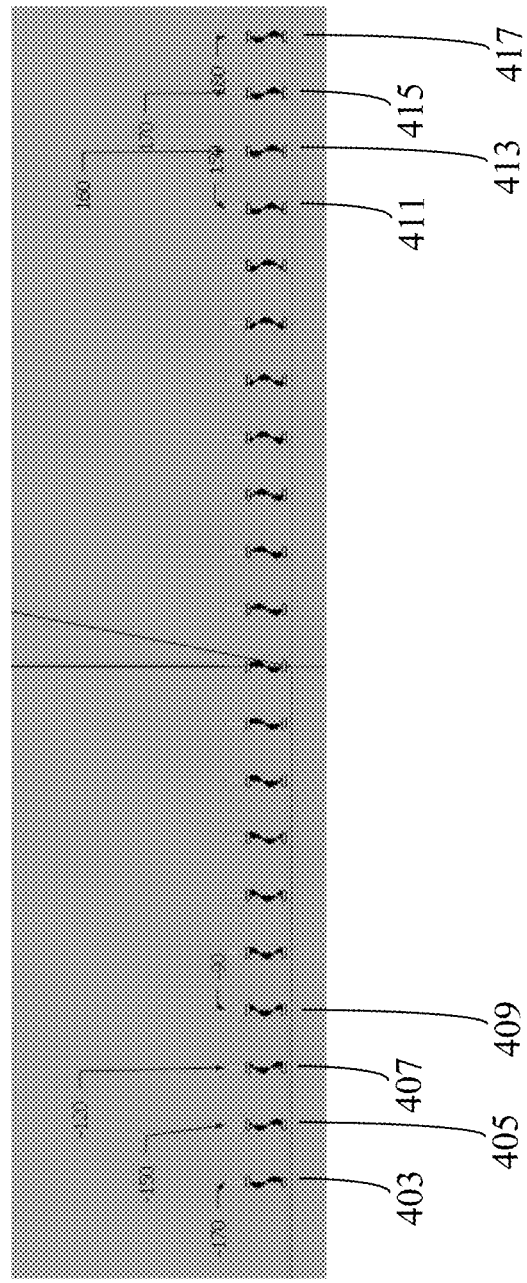
FIG. 4 shows a catheter twist-indicating pattern detected in an angiogram indicating different catheter orientation in a 360 degree rotation range, according to invention principles.

FIG. 4 shows a catheter twist-indicating pattern detected in an angiogram indicating different catheter orientation in a 360 degree rotation range. The catheter twist-indicating pattern appears differently depending on angle of catheter rotation in a 2D angiogram enabling automatic identification of different catheter twist angle from a 2D angiogram provided the angiogram shows a catheter side view with reasonable clarity. Patterns 403, 405, 407, 409, 411, 413, 415 and 417 indicate catheter twist angles −170, −150, −120, −90, 150, 160, 170 and 180 degrees respectively, for example.

Figure 5:
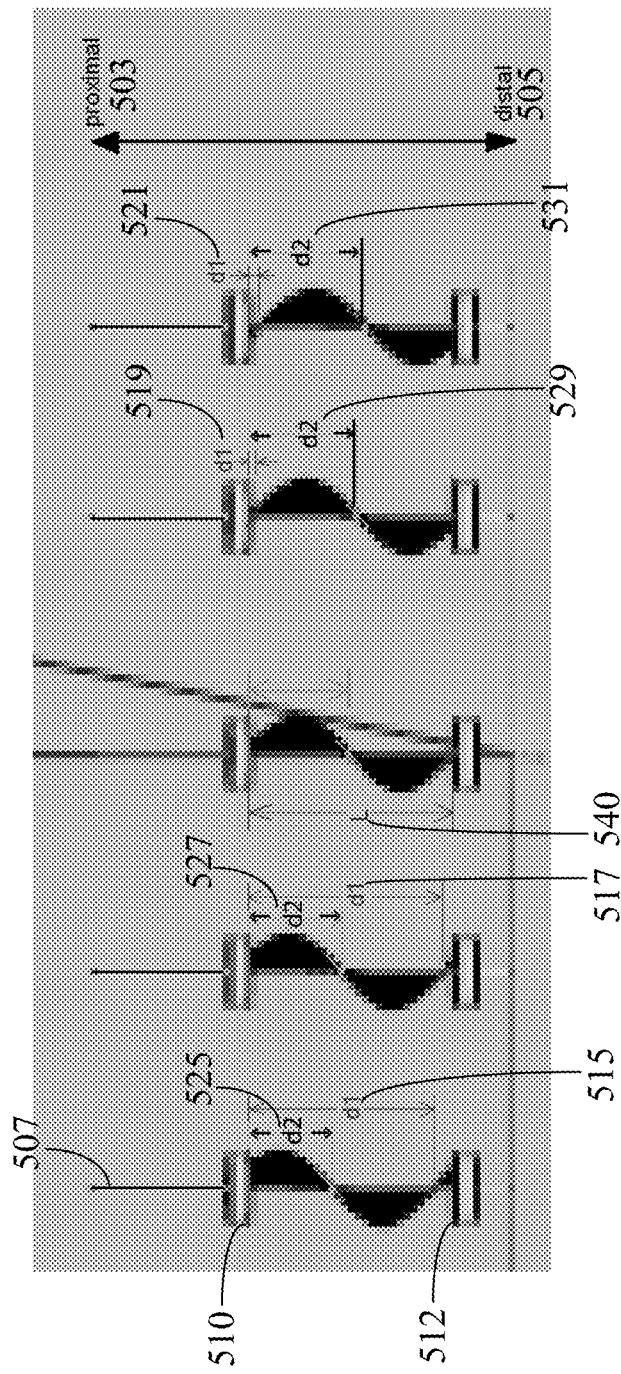
FIG. 5 shows system automatic analysis of an X-ray image to determine twist angle of a catheter from a twist-indicating pattern detected in an angiogram, according to invention principles.

FIG. 5 shows system automatic analysis of an X-ray image to determine twist angle of a catheter from a twist-indicating pattern detected in an angiogram. System 10 (FIG. 1) automatically analyzes an X-ray image to determine a twist angle of the catheter. Imaging system 25 images a catheter positioned with proximal portion pointing to the top of the image 503 and distal portion pointing downwards 505. Image data processor 15 performs feature extraction on image data to identify the axis of the catheter (a guide wire) 507, the two ends of the twist indicator pattern 510, 512 and the narrowing points of the twist pattern, on an X-ray image. Processor 15 employs a twist pattern detection function by pattern edge detection using a known edge detection function based on adjacent pixel luminance transitions and by pattern shape matching and comparison with predetermined twist angle associated patterns using iterative scaling, rotation and translation operations, for example.

Processor 15 automatically analyzes an image acquired by system 25 using the twist pattern detection function to identify d1 and L. Measurement d1 (515, 517, 519, 521), is defined as a distance from a proximal end of the twist indicator pattern to a narrowing of the pattern, where the edge of the twist transitions across an axis of the catheter from upper-left to lower-right. Measurement d2 (525, 527, 529, 531), is defined as a distance from the proximal end of the indicator to a narrowing of the indicator, where the edge of the twist transitions across an axis from upper-right to lower-left. L 540 is a constant representing the length of the twist indicator pattern. The value of L 540 is predetermined and known in a calibrated X-ray angiogram.

The catheter twist angle γ is automatically calculated by processor 15 as, $$\gamma = \begin{cases} \dfrac{d1}{L} \times 360.0, & 0 < d1 \leq L/2.0 \\ 360.0 - \dfrac{d1}{L} \times 360.0, & L/2.0 < d1 < L \end{cases}$$

The catheter twist angle range is −180 to 180 degrees. Data padding is used to extend this range if needed, in order to make the twist angle continuous and smooth among consecutive frames.

The higher the resolution of an image analyzed by processor 15 to detect a twist pattern, the more accurate the resulting detected catheter twist angle. In a coronary catheterization, a typical catheter is 2.0 mm in diameter corresponding to approximately 10 pixels in an angiogram image. This is sufficient for processor 15 to give a reasonable twist angle calculation value. In operation, IVUS catheter 29 having a twist indicating radio-opaque pattern, acquires IVUS image data and X-ray imaging system 25 concurrently acquires an X-ray image in which catheter 29 is depicted. Image data processor 15 processes the X-ray image using a pattern edge detection function to determine parameters including the axis of catheter 29 (a guide wire), the two ends of the twist indicator pattern, the edge of the twist pattern, the intersection points between the edge of the twist and the axis and a slope or direction of the edge at the intersection points. Image data processor 15 uses the determined parameters to determine the distances L, d1, d2. Processor 15 records the γ twist angle value together with the corresponding IVUS image data for use in further analysis.

Figure 6:
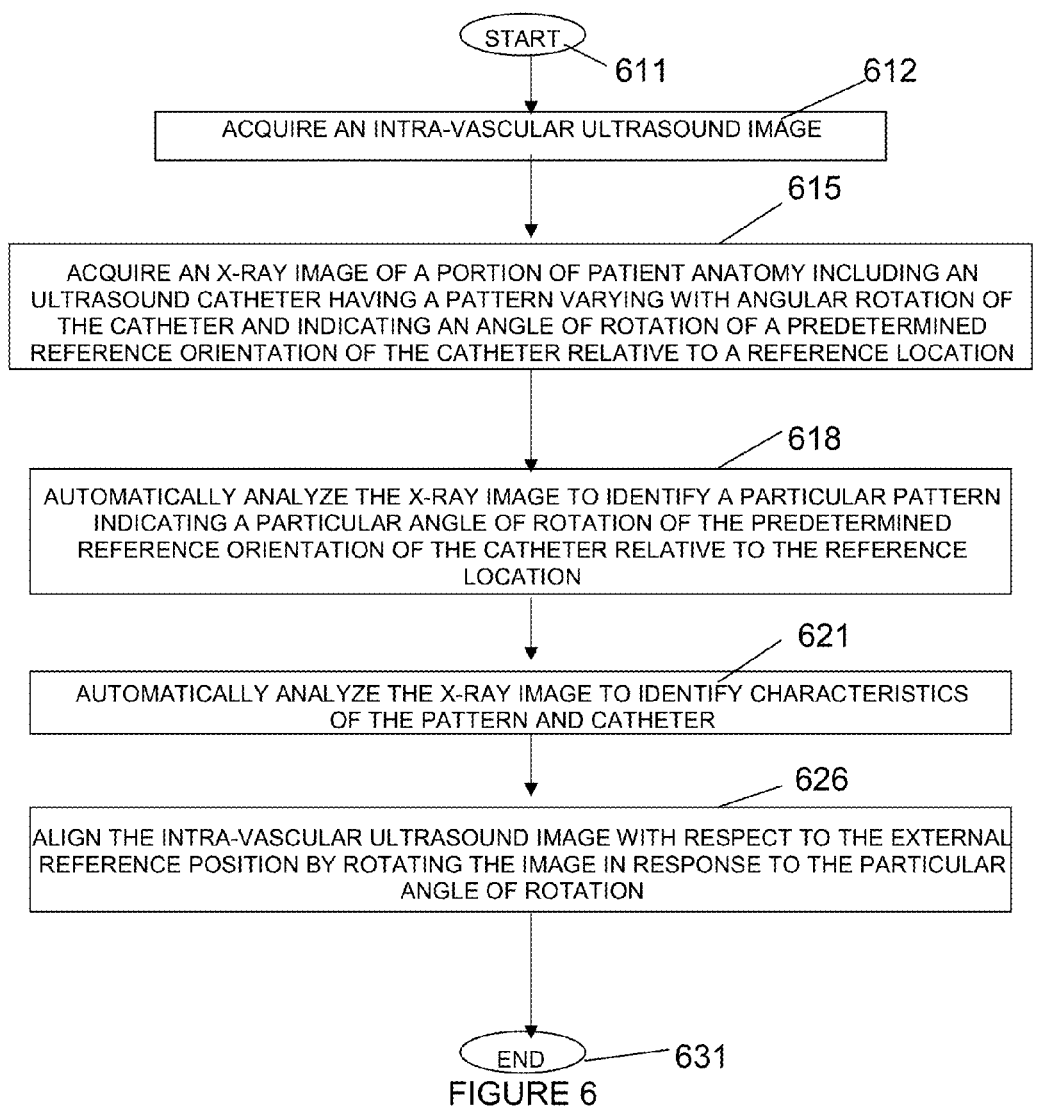
FIG. 6 shows a flowchart of a process employed by an ultrasound catheter system supporting orientation and display of intra-vascular ultrasound imaging data, according to invention principles.

FIG. 6 shows a flowchart of a process employed by ultrasound catheter system 10 (FIG. 1) supporting orientation and display of intra-vascular ultrasound imaging data. IVUS catheter 29 in step 612 following the start at step 611, acquires an intra-vascular ultrasound image. In step 615, acquisition processor 23 acquires an X-ray image of a portion of patient anatomy showing ultrasound catheter 29 and produced by imaging system 25. The ultrasound catheter in the X-ray image shows a pattern varying with angular rotation of the catheter and indicates an angle of rotation of a predetermined reference orientation of the catheter relative to a reference location. In one embodiment the reference location comprises a location of an X-ray radiation source and the pattern comprises a helical pattern. In step 618, image data processor 15 automatically analyzes the X-ray image to identify a particular pattern indicating a particular angle of rotation of the predetermined reference orientation of the catheter relative to the reference location.

Image data processor 15 in step 621 automatically analyzes the X-ray image to identify characteristics of the pattern and catheter 29. Specifically, the image data processor automatically analyzes the X-ray image to identify, an axis of the catheter, the two ends of the pattern, an edge of the pattern and an intersection point of the edge with an axis of the catheter, a distance between an edge of the pattern and an intersection point of the edge with an axis of the catheter and a slope or direction of the edge at the intersection point. Processor 15 uses the distance in determining the angle of rotation. Processor 15 in step 626 aligns the intra-vascular ultrasound image with respect to the external reference position by rotating the image in response to the particular angle of rotation. The process of FIG. 6 terminates at step 631.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. Computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of the FIGS. 1-6 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. An IVUS catheter has a particular radio-opaque pattern enabling detection of catheter rotation angle with respect to an X-ray imaging source using an X-ray image of the catheter in a patient and the angle is used for aligning intravascular ultrasound (IVUS) images acquired by a catheter during advancement or retraction of the catheter in a vessel, for example. Further, the processes and applications may, in alternative embodiments, be located on one or more (e.g., distributed) processing devices on a network linking the units of FIG. 1. Any of the functions and steps provided in FIGS. 1-6 may be implemented in hardware, software or a combination of both. No claim element herein is to be construed under the provisions of 35 U.S.C. 112, sixth paragraph, unless the element is expressly recited using the phrase "means for."

What is claimed is:

1. An ultrasound catheter system supporting orientation and display of intra-vascular ultrasound imaging data, comprising:
    one or more imaging devices configured to perform image acquisition of the patient anatomy;
    an ultrasound catheter configured to be placed in the patient anatomy and acquire ultrasound images, the catheter comprising:
       a body having a pattern of radio-opaque material, said pattern:
          varying with angular rotation of said catheter; and
          indicating an angle of rotation of a predetermined reference orientation of said catheter relative to a reference location, so that an X-ray image of said catheter body indicates said pattern and said pattern is analyzable by an image data processor to determine said angle of rotation; and
    an image data processor configured to automatically analyze said X-ray image to identify a distance between a proximal end of the pattern and an intersection point of an edge of the pattern and an axis of said catheter; and
       said image data processor uses said distance in determining said angle of rotation.

2. A system according to claim 1, wherein
said pattern of radio-opaque material comprises a helical pattern.

3. A system according to claim 2, wherein
said pattern is located on the external surface of the catheter body and said
image data processor is configured to automatically analyze said X-ray image to identify
two ends of said pattern.

4. A system according to claim 1, wherein
said image data processor automatically analyzes said X-ray image to identify,
a slope or direction of said edge at said intersection point.

5. A system according to claim 1, wherein said reference location comprises a location of an X-ray radiation source.

6. A system for orientation and display of intra-vascular ultrasound imaging data, comprising:
an acquisition processor for acquiring an X-ray image of a portion of patient anatomy showing an ultrasound catheter, said ultrasound catheter in said X-ray image showing a pattern varying with angular rotation of said catheter and indicating an angle of rotation of a predetermined reference orientation of said catheter relative to a reference location; and
an image data processor for automatically analyzing said X-ray image to identify said pattern indicating said angle of rotation of said predetermined reference orientation of said catheter relative to said reference location, wherein
said image data processor automatically analyzes said X-ray image to identify a distance between a proximal end of the pattern and an intersection point of the edge and an axis of said catheter, and
said image data processor uses said distance in determining said angle of rotation.

7. A system according to claim 6, wherein
said ultrasound catheter acquires an intra-vascular ultrasound image and
said image data processor aligns said intra-vascular ultrasound image with respect to the external reference position by rotating said image in response to said particular angle of rotation.

8. A system according to claim 6, wherein
said pattern comprises a helical pattern.

9. A system according to claim 6, wherein
said image data processor automatically analyzes said X-ray image to identify two ends of said pattern.

10. A system according to claim 6, wherein
said image data processor automatically analyzes said X-ray image to identify a slope or direction of said edge at said intersection point.

11. A system according to claim 6, wherein
said reference location comprises a location of an X-ray radiation source.

12. A method for orientation and display of intra-vascular ultrasound imaging data, comprising the activities of:
acquiring an X-ray image, by an acquisition processor, of a portion of patient anatomy showing an ultrasound catheter, said ultrasound catheter in said X-ray image showing a pattern varying with angular rotation of said catheter and indicating an angle of rotation of a predetermined reference orientation of said catheter relative to a reference location; and
automatically analyzing said X-ray image, by an image data processor, to identify said pattern indicating said angle of rotation of said predetermined reference orientation of said catheter relative to said reference location; wherein said automatic analysis identifies a distance between a proximal end of the pattern and an intersection point of the edge and an axis of said catheter, and said distance is used to determine said angle of rotation.

13. A method according to claim 12, including the activity of
acquiring an intra-vascular ultrasound image and
aligning said intra-vascular ultrasound image with respect to the external reference position by rotating said image in response to said angle of rotation.

14. A method according to claim 12, wherein
said pattern comprises a helical pattern.

* * * * *